(12) United States Patent
Graf et al.

(10) Patent No.: US 7,087,773 B2
(45) Date of Patent: Aug. 8, 2006

(54) GROUP 4 METAL COMPLEXES CONTAINING 4-ARYL-SUBSTITUTED, TRICYCLIC INDENYL DERIVATIVES

(75) Inventors: David D. Graf, Midland, MI (US); Roger L. Kuhlman, South Charleston, WV (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/520,378

(22) PCT Filed: May 22, 2003

(86) PCT No.: PCT/US03/16265

§ 371 (c)(1), (2), (4) Date: Jan. 3, 2005

(87) PCT Pub. No.: WO2004/013149

PCT Pub. Date: Feb. 12, 2004

(65) Prior Publication Data

US 2005/0261510 A1    Nov. 24, 2005

Related U.S. Application Data

(60) Provisional application No. 60/400,489, filed on Aug. 2, 2002, provisional application No. 60/400,398, filed on Jul. 31, 2002.

(51) Int. Cl.
*C07F 17/00* (2006.01)
*B01J 31/00* (2006.01)
*C08F 4/44* (2006.01)

(52) U.S. Cl. .......................... 556/11; 556/12; 556/19; 556/21; 556/22; 526/126; 526/160; 526/943; 502/103; 502/117; 502/152

(58) Field of Classification Search .................. 556/11, 556/12, 19, 21, 22; 526/160, 943, 126; 502/103, 502/117, 152
See application file for complete search history.

(56) References Cited

U.S. PATENT DOCUMENTS 5,965,756 A    10/1999    McAdon et al. .............. 556/11

*Primary Examiner*—Porfirio Nazario-Gonzalez

(57) ABSTRACT

Group 4 metal constrained geometry complexes comprising tricyclic 4-arylsubstituted indenyl ligands, especially 1,5,6,7-tetrahydro-4-aryl-s-indacen-1-yl ligands, catalytic derivatives thereof, processes for preparing the same and their use as components of olefin polymerization catalysts are disclosed.

6 Claims, No Drawings

GROUP 4 METAL COMPLEXES CONTAINING 4-ARYL-SUBSTITUTED, TRICYCLIC INDENYL DERIVATIVES

CROSS REFERENCE STATEMENT

This application claims the benefit of U.S. Provisional Application Nos. 60/400,489, filed Aug. 2, 2002 and 60/400,398, filed Jul. 31, 2002.

BACKGROUND OF THE INVENTION

This invention relates to a class of Group 4 metal complexes and to polymerization catalysts derived therefrom that are particularly suitable for use in a polymerization process for preparing homopolymers and copolymers of olefins or diolefins, including copolymers comprising two or more olefins or diolefins such as copolymers comprising a monovinyl aromatic monomer and ethylene or copolymers comprising ethylene, propylene and a conjugated diene.

In U.S. Pat. No. 5,965,756 there were disclosed certain Group 4 metal fused ring, indenyl complexes that were usefully employed as olefin polymerization catalyst components. The present complexes are species within this previously disclosed genera of Group 4 metal compounds.

SUMMARY OF THE INVENTION

According to the present invention there are provided metal complexes corresponding to the formula (I):

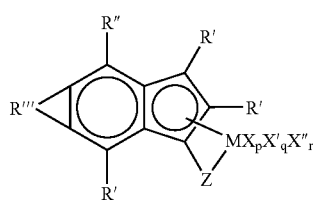

(I)

where M is titanium, zirconium or hafnium in the +2, +3 or +4 formal oxidation state;

R' independently each occurrence is hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R' group having up to 40 nonhydrogen atoms, and optionally two or more of the foregoing groups may together form a divalent derivative;

R'' independently each occurrence is a $C_{6-12}$ aryl group;

R''' is a divalent hydrocarbylene- or substituted hydrocarbylene group forming a fused system with the remainder of the metal complex, said R''' containing from 1 to 30 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

Preferred complexes according to the present invention there are metal complexes corresponding to the formula (II):

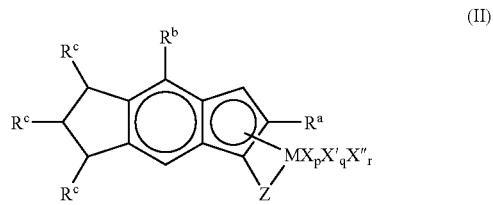

(II)

where M is titanium, zirconium or hafnium in the +2, +3 or +4 formal oxidation state;

$R^a$ independently each occurrence is hydrogen, $C_{1-10}$ alkyl, aralkyl or cycloalkyl, preferably methyl or benzyl;

$R^b$ is a $C_{6-12}$ aryl group;

$R^c$ independently each occurrence is hydrogen, $C_{1-6}$ alkyl, or cycloalkyl, preferably each occurrence $R^c$ is hydrogen;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

The above complexes may exist as isolated crystals optionally in pure form or as a mixture with other complexes, in the form of a solvated adduct, optionally in a solvent, especially an organic liquid, as well as in the form of a dimer or chelated derivative thereof, wherein the chelating agent is an organic material such as ethylenediaminetetraacetic acid (EDTA).

Also, according to the present invention, there is provided a catalyst for olefin polymerization comprising:

A. 1) a metal complex of formula (I) or (II), and
   2) an activating cocatalyst, the molar ratio of 1) to 2) being from 1:10,000 to 100:1, or B. the reaction product formed by converting a metal complex of formula (I) or (II) to an active catalyst by use of an activating technique.

Further according to the present invention there is provided a process for the polymerization of olefins comprising contacting one or more $C_{2-20}$ α-olefins under polymerization conditions with a catalyst comprising:

A. 1) a metal complex of formula (I) or (II), and
   2) an activating cocatalyst, the molar ratio of 1) to 2) being from 1:10,000 to 100:1, or B. the reaction product formed by converting a metal complex of formula (I) or (II) to an active catalyst by use of an activating technique.

Use of the present catalysts and processes results in the highly efficient production of high molecular weight olefin polymers over a wide range of polymerization conditions, and especially at elevated temperatures. They are especially useful for the formation of ethylene homopolymers, copolymers of ethylene and one or more α-olefins other than ethylene, copolymers of ethylene, propylene and a diene (EPDM copolymers), copolymers of ethylene and styrene (ES polymers), copolymers of ethylene, styrene, and a diene (ESDM polymers), and copolymers of ethylene, propylene and styrene (EPS polymers). The use of the complexes, especially those wherein the metal is in the +2 formal oxidation state in continuous solution polymerizations surprisingly results in formation of polymers, especially EPDM terpolymers having extremely high molecular weights.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

Compared to complexes lacking in the present aryl group substituted at the 4-position of the substituted indenyl ligand, the present complexes demonstrate greater activity and incorporate increased quantities of α-olefin or other comonomer into ethylene copolymers. Accordingly, catalyst compositions including the present metal complexes are capable of producing ethylene/α-olefin copolymers in greater efficiency and/or are capable of forming copolymers of lower density, due to the fact that such copolymers have increased levels of incorporation of the α-olefin comonomer.

DETAILED DESCRIPTION OF THE INVENTION

All reference to the Periodic Table of the Elements herein shall refer to the Periodic Table of the Elements, published and copyrighted by CRC Press, Inc., 1999. Also, any reference to a Group or Groups shall be to the Group or Groups as reflected in this Periodic Table of the Elements using the IUPAC system for numbering groups. For purposes of United States patent practice, the contents of any patent, patent application or publication identified herein are hereby incorporated by reference in their entirety, especially with respect to the disclosure of synthetic techniques and general knowledge in the art. The term "comprising" when used herein with respect to a composition, mixture or process is not intended to exclude the additional presence of any other compound, component or step.

Olefins as used herein are $C_{2-100,000}$ aliphatic or aromatic compounds containing vinylic unsaturation, as well as cyclic compounds such as cyclobutene, cyclopentene, and norbornene, including norbornene substituted in the 5 and 6 position with $C_{1-20}$ hydrocarbyl groups. Also included are mixtures of such olefins as well as mixtures of such olefins with $C_{4-40}$ diolefin compounds. Examples of the latter compounds include ethylidenenorbornene, 1,4-hexadiene, and norbornadiene. Long chain vinyl terminated monomers may be formed during the polymerization process, for example by the phenomenon of β-hydride elimination of a proton from a growing polymer chain. This process results in incorporation of extremely long chains into the resulting polymer, i.e. long chain branching. The catalysts and processes herein are especially suited for use in preparation of ethylene/propylene, ethylene/1-butene, ethylene/1-hexene, ethylene/styrene, and ethylene/1-octene copolymers as well as terpolymers of ethylene, propylene and a nonconjugated diene, referred to as EPDM polymers, terpolymers of ethylene, propylene and styrene, referred to as EPS polymers, or terpolymers of ethylene, styrene and a non-conjugated diene, referred to as ESDM polymers.

Monovinyl aromatic monomers for use herein include $C_{8-20}$ aryl substituted ethylene compounds having the formula:

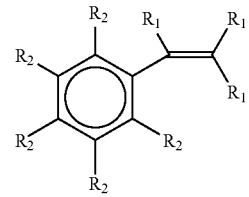

wherein:
$R_1$ independently each occurrence is hydrogen or $C_{1-4}$ alkyl, and
$R_2$ independently each occurrence is $R_1$ or halo.

In the metal complexes, preferred X' groups are carbon monoxide; phosphines, especially trimethylphosphine, triethylphosphine, triphenylphosphine and bis(1,2-dimethylphosphino)ethane; P(OR)₃, wherein R is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40 carbon atoms. Complexes including such neutral diene X' groups are those wherein the metal is in the +2 formal oxidation state.

Further in reference to the metal complexes (I) or (II), X preferably is selected from the group consisting of halo, hydrocarbyl, silyl, and N,N-dialkylamino substituted hydrocarbyl. The number of X groups depends on the oxidation state of M, whether Z is divalent or not and whether any neutral diene groups or divalent X" groups are present. The skilled artisan will appreciate that the quantity of the various substituents and the identity of Z are chosen to provide charge balance, thereby resulting in a neutral metal complex. For example, when Z is divalent, and r is zero, p is two less than the formal oxidation state of M. When Z contains one neutral two electron coordinate-covalent bonding site, and M is in a formal oxidation state of +3, p may equal zero and r equal 1, or p may equal 2 and r equal zero. In a final example, if M is in a formal oxidation state of +2, Z may be a divalent ligand group, p and r may both equal zero and one neutral ligand group may be present.

Preferred coordination complexes used according to the present invention are complexes corresponding to the formula:

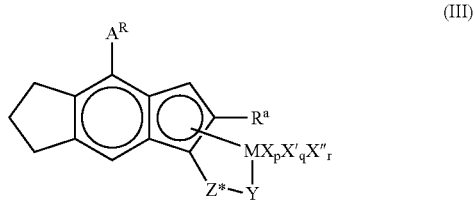

(III)

wherein:
$A^R$ is phenyl or naphthalenyl;
$R^a$ is methyl or benzyl;
M is titanium;

Y is —O—, —S—, —NR*—, —PR*—; —NR$_2$*, or —PR$_2$*;

Z* is SiR*$_2$, CR*$_2$, SiR*$_2$SiR*$_2$, CR*$_2$CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 24 non-hydrogen atoms, and optionally, two R* groups from Z (when R* is not hydrogen), or an R* group from Z and an R* group from Y form a ring system;

X, X' and X" are as previously defined;

p is 0, 1 or 2;

q is zero or 1; and r is zero or 1; and when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl) phosphino-substituted derivatives thereof, said X group having up to 30 nonhydrogen atoms, when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

Most preferred metal complexes are those according to the previous formula (III), wherein M, X, X', X", R' R", Z*, Y, p, q and r are as previously defined, and:

when p is 2, q and r are zero, M is in the +4 formal oxidation state, and X is independently each occurrence methyl, benzyl, or halide;

when p and q are zero, r is one, and M is in the +4 formal oxidation state, X" is a 1,4-butadienyl group that forms a metallocyclopentene ring with M, when p is 1, q and r are zero, M is in the +3 formal oxidation state, and X is 2-(N,N-dimethylamino)benzyl; and when p and r are 0, q is 1, M is in the +2 formal oxidation state, and X' is 1,4-diphenyl-1,3-butadiene or 1,3-pentadiene.

Illustrative metal complexes that may be employed in the practice of the present invention include:

2-methyl-4-phenyl-s-1,5,6,7-tetrahydroindacen-1-yl Complexes (t-butylamido)dimethyl(2-methyl-4-phenyl-η$^5$-s-1,5,6,7-tetrahydroindacen-1-yl)silanetitanium (II) 1,4-diphenyl-1,3-butadiene, (t-butylamido)dimethyl(2-methyl-4-phenyl-η$^5$-s-1,5,6,7-tetrahydroindacen-1-yl)silanetitanium (II) 1,3-pentadiene, (t-butylamido)dimethyl(2-methyl-4-phenyl-η$^5$-s-1,5,6,7-tetrahydroindacen-1-yl)silanetitanium (III) 2-(N,N-dimethylamino)benzyl, (t-butylamido)dimethyl(2-methyl-4-phenyl-η$^5$-s-1,5,6,7-tetrahydroindacen-1-yl)silanetitanium (IV) dimethyl, (t-butylamido)dimethyl(2-methyl-4-phenyl-η$^5$-s-1,5,6,7-tetrahydroindacen-1-yl)silanetitanium (IV) dibenzyl, (i-propylamido)dimethyl(2-methyl-4-phenyl-η$^5$-s-1,5,6,7-tetrahydroindacen-1-yl)silanetitanium (IV) dimethy (benzylamido)dimethyl(2-methyl-4-phenyl-η$^5$-s-5,6,7-1,5,6,7-tetrahydroindacen-1-yl)silanetitanium (IV) dimethyl, (cyclohexylamido)dimethyl(2-methyl-4-phenyl-η$^5$-s-1,5,6,7-tetrahydroindacen-1-yl)silanetitanium (IV) dimethyl, 2-benyzl-4-phenyl-s-1,5,6,7-tetrahydroindacen-1-yl Complexes (t-butylamido)dimethyl(2-benzyl-4-phenyl-η$^5$-s-1,5,6,7-tetrahydroindacen-1-yl)silanetitanium (II) 1,4-diphenyl-1,3-butadiene, (t-butylamido)dimethyl(2-benzyl-4-phenyl-η$^5$-s-1,5,6,7-tetrahydroindacen-1-yl)silanetitanium (II) 1,3-pentadiene, (t-butylamido)dimethyl(2-benzyl-4-phenyl-η$^5$-s-1,5,6,7-tetrahydroindacen-1-yl)silanetitanium (III) 2-(N,N-dimethylamino)benzyl, (t-butylamido)dimethyl(2-benzyl-4-phenyl-η$^5$-s-1,5,6,7-tetrahydroindacen-1-yl)silanetitanium (IV) dimethyl, (t-butylamido)dimethyl(2-benzyl-4-phenyl-η$^5$-s-1,5,6,7-tetrahydroindacen-1-yl)silanetitanium (IV) dibenzyl, (i-propylamido)dimethyl(2-benzyl-4-phenyl-η$^5$-s-1,5,6,7-tetrahydroindacen-1-yl)silanetitanium (IV) dimethyl, (benzylamido)dimethyl(2-benzyl-4-phenyl-η$^5$-s-1,5,6,7-tetrahydroindacen-1-yl)silanetitanium (IV) dimethyl, (cyclohexylamido)dimethyl(2-benzyl-4-phenyl-η$^5$-s-1,5,6,7-tetrahydroindacen-1-yl)silanetitanium (IV) dimethyl, 2-methyl-4-(1-naphthalenyl)-s-1,5,6,7-tetrahydroindacen-1-yl-Complexes (t-butylamido)dimethyl(2-methyl-4-(1-naphthalenyl)-η$^5$-s-1,5,6,7-tetrahydroindacen-1-yl)silanetitanium (II) 1,4-diphenyl-1,3-butadiene, (t-butylamido)dimethyl(2-methyl-4-(1-naphthalenyl)-η$^5$-s-1,5,6,7-tetrahydroindacen-1-yl)silanetitanium (II) 1,3-pentadiene, (t-butylamido)dimethyl(2-methyl-4-(1-naphthalenyl)-η$^5$-s-1,5,6,7-tetrahydroindacen-1-yl)silanetitanium (III) 2-(N,N-dimethylamino)benzyl, (t-butylamido)dimethyl(2-methyl-4-(1-naphthalenyl)-η$^5$-s-1,5,6,7-tetrahydroindacen-1-yl)silanetitanium (IV) dimethyl, (t-butylamido)dimethyl(2-methyl-4-(1-naphthalenyl)-η$^5$-s-1,5,6,7-tetrahydroindacen-1-yl)silanetitanium (IV) dibenzyl, (i-propylamido)dimethyl(2-methyl-4-(1-naphthalenyl)-η$^5$-s-1,5,6,7-tetrahydroindacen-1-yl)silanetitanium (IV) dimethyl, (benzylamido)dimethyl(2-methyl-4-(1-naphthalenyl)1-η$^5$-s-1,5,6,7-tetrahydroindacen-1-yl)silaneitanium (IV) dimethyl, (cyclohexylamido)dimethyl(2-methyl-4-(1-naphthalenyl)-η$^5$-s-1,5,6,7-tetrahydroindacen-1-yl)silanetitanium (IV) dimethyl, 2-benzyl-4-(1-naphthalenyl)-s-1,5,6,7-tetrahydroindacen-1-yl Complexes (t-butylamido)dimethyl(2-benzyl-4-(1-naphthalenyl)-η$^5$-s-1,5,6,7-tetrahydroindacen-1-yl)silanetitanium (II) 1,4-diphenyl-1,3-butadiene, (t-butylamido)dimethyl(2-benzyl-4-(1-naphthalenyl)-η$^5$-s-1,5,6,7-tetrahydroindacen-1-yl)silanetitanium (II) 1,3-pentadiene, (t-butylamido)dimethyl(2-benzyl-4-(1-naphthalenyl)-,$\eta^5$-s-1,5,6,7-tetrahydroindacen-1-yl)silanetitanium (III) 2-(N,N-dimethylamino)benzyl, (t-butylamido)dimethyl(2-benzyl-4-(1-naphthalenyl)-$\eta^5$-s-1,5,6,7-tetrahydroindacen-1-yl)silanetitanium (IV) dimethyl, (t-butylamido)dimethyl(2-benzyl-4-(1-naphthalenyl)-$\eta^5$-s-1,5,6,7-tetrahydroindacen-1-yl)silanetitanium (IV) dibenzyl, (i-propylamido)dimethyl(2-benzyl-4-(1-naphthalenyl)-$\eta^5$-s-1,5,6,7-tetrahydroindacen-1-yl)silanetitanium (IV) dimethyl, (benzylamido)dimethyl(2-benzyl-4-(1-naphthalenyl)1-$\eta^5$-s-1,5,6,7-tetrahydroindacen-1-yl)silanetitanium (IV) dimethyl, and (cyclohexylamido)dimethyl(2-benzyl-4-(1-naphthalenyl)-$\eta^5$-s-1,5,6,7-tetrahydroindacen-1-yl)silanetitanium (IV) dimethyl.

The complexes can be prepared by use of well known synthetic techniques. Optionally a reducing agent can be employed to produce the lower oxidation state complexes. The syntheses are conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are group 1 or 2 metal hydrocarbyl compounds having from 1 to 20 carbons in each hydrocarbyl group, such as, sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The neutral diene complexes are prepared by contacting the corresponding complex in the +4 or +3 oxidation state with a neutral diene in the presence of a reducing agent, preferably a group 1 or 2 metal alkyl derivative having from 1 to 6 carbons in each alkyl group in an inert diluent. It has been found that the use of from 1.0 to 2.0 equivalents of the diene in the foregoing reaction gives improved yields and purity of the desired diene complex compared to the use of larger quantities of the diene. In addition, heating the reaction mixture prior to addition of the conjugated diene reactant, preferably to a temperature from 50 to 95° C., gives a further improvement in yield and purity.

The resulting Group 4 metal complexes are activated to form the actual catalyst composition by combination with a cocatalyst, preferably an aluminoxane, a cation forming cocatalyst, or a combination thereof and desirably employed to polymerize olefins or combinations of olefins, especially ethylene, propylene, 1-butene, 1-hexene, 1-octene; mixtures thereof; mixtures of the foregoing monomers with vinylaromatic monomers or conjugated or non-conjugated dienes; and mixtures of all of the foregoing monomers. In a preferred process ethylene and one or more $C_{3-8}$ α-olefins or styrene and optionally a conjugated or non-conjugated diene are interpolymerized The process is characterized by low temperatures, typically from 25 to 50° C. and pressures from atmospheric to 10 MPa.

Suitable alumoxanes for use herein include polymeric or oligomeric alumoxanes, especially methylalumoxane, triisobutyl aluminum modified methylalumoxane, or isobutylalumoxane; neutral Lewis acid modified polymeric or oligomeric alumoxanes, such as the foregoing alkylalumoxanes modified by addition of a $C_{1-30}$ hydrocarbyl substituted Group 13 compound, especially a tri(hydrocarbyl)aluminum- or tri(hydrocarbyl)boron compound, or a halogenated (including perhalogenated) derivative thereof, having from 1 to 10 carbons in each hydrocarbyl or halogenated hydrocarbyl group, more especially a perfluorinated tri(aryl)boron compound or a perfluorinated tri(aryl)aluminum compound.

The Group 4 metal complexes may also be rendered catalytically active by combination with a cation forming cocatalyst, such as those previously known in the art for use with Group 4 metal olefin polymerization complexes. Suitable cation forming cocatalysts for use herein include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating cocatalysts and activating techniques have been previously taught with respect to different metal complexes for olefin polymerizations in the following references: EP-A-277,003, U.S. Pat. Nos. 5,153,157, 5,064,802, 5,321,106, 5,721,185, 5,350,723, 5,425,872, 5,625,087, 5,883,204, 5,919,983, 5,783,512, and 5,965,756.

EXAMPLES

The skilled artisan will appreciate that the invention disclosed herein may be practiced in the absence of any component which has not been specifically disclosed. The following examples are provided as further illustration of the invention and are not to be construed as limiting. All syntheses were performed under dry nitrogen atmosphere using a combination of glove box and high vacuum techniques. Unless stated to the contrary all parts and percentages are expressed on a weight basis. The term "overnight", if used, refers to a time of approximately 16–18 hours, the term "room temperature", refers to a temperature of 20–25° C., and the term "mixed alkanes" refers to a commercially obtained mixture of $C_{6-9}$ aliphatic hydrocarbons available under the trade designation Isopar E®, from Exxon Chemicals Inc. In the event the name of a compound herein does not conform to the structural representation thereof, the structural representation shall control.

Example 1

Synthesis of: dichloro[N-(1,1-dimethylethyl)-1,1-dimethyl-[1,2,3,3a,8a-η)-1,5,6,7-tetrahydroindacen-2-methyl-4-phenyl-s-indacen-1-yl]silanaminato(2-)-N] titanium

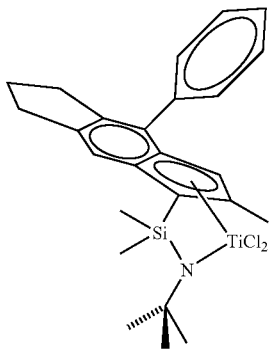

1a) Preparation of 3,5,6,7-tetrahydro-2-methyl-s-hydraindacen-1(2H)-one

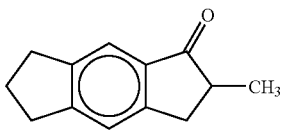

Indan (91.8 mL, 0.75 moles) and 2-bromoisobutyryl bromide (92.7 mL, 0.75 moles) were stirred in $CH_2Cl_2$ (600 mL) at 0° C. as $AlCl_3$ (300.6 g, 2.25 moles) was added slowly as a solid under a nitrogen flow. This mixture was then allowed to stir for 6 hours at 20–25° C. After the reaction period the mixture was poured over ice and allowed to sit 16 hours. The mixture was then decanted into a separatory funnel and the remaining salts washed well with $CH_2Cl_2$. The organic layer was then separated and the volatiles removed resulting in the isolation of a dark oil. Vacuum distillation resulted in the isolation of the desired product as a yellow oil (120 g, 86 percent).

1b) Preparation of 3,5,6,7-tetrahydro-2-methyl-4-bromo-s-hydraindacen-1(2H)-one

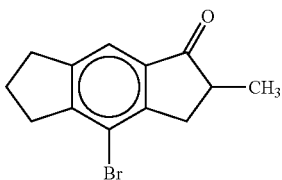

3,5,6,7-tetrahydro-2-methyl-s-hydraindacen-1(2H)-one (50.24 g, 0.270 moles) was gradually added over one hour with stirring to an oven dried, nitrogen purged, 1 L glass round bottom flask containing $AlCl_3$ (99.842 g, 0.749 mol). Bromine (13.8 mL, 0.268 mol) was added via a dropping funnel over 45 minutes. The resulting red mixture was heated with stirring to 76° C. for 45 minutes. The reaction mixture was cooled to room temperature and poured onto ice (1500 g) containing concentrated hydrochloric acid (50 mL) and then extracted with diethylether (4×200 mL). The organic fractions were combined, washed with aqueous $NaHCO_3$ and water, dried over $MgSO_4$, and dried under dynamic vacuum.

The mixture was then fractionally distilled. The fraction obtained at 135–142° C.@15 mTorr was found to be the desired product in greater than 90 percent purity. Yield: 20.4 g, 54 percent.

1c) Preparation of 3,5,6,7-tetrahydro-2-methyl-4-phenyl-s-hydraindacen-1(2H)-one

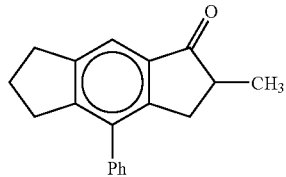

100 mL of a 0.22 M ethlyene glycol dimethylether solution of 5,6,7-tetrahydro-2-methyl-4-bromo-s-indacen-1-one (22 mmol) was gradually added with stirring to an oven dried, nitrogen purged, 250 mL glass round bottom flask containing $Pd(P(C_6H_5)_3)_4$ (0.19 g, 0.16 mmol), $Na_2CO_3$ (3.37 g, 31.8 mmol) and $(C_6H_5)B(OH)_2$. Water (25 mL) was added and the mixture was heated to reflux while being stirred.

After 16 hours the solvent was removed under reduced pressure and the remaining yellow mixture extracted with diethylether (3×60 mL). The organic layers were combined, dried over $MgSO_4$ and filtered through silica. Remaining solvent was removed under dynamic vacuum. Due to impurities in the product, the mixture was again combined in diethylether, washed, filtered, dried and dissolved in hot hexane (125 mL) followed by filtration and devolatilization. Final purification using column chromatography and 5:1 vol.:vol. mixture of hexane/methyl acetate elutent resulted in 2.48 g (43 percent) of product with >90 percent purity by $^1H$ NMR.

1d) Preparation of 3,5,6,7-tetrahydro-2-methyl-4-phenyl-s-hydraindacen-1(2H)-ol

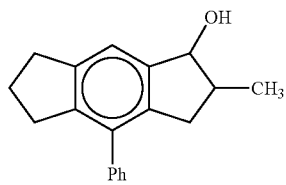

3,5,6,7-tetrahydro-2-methyl-4-phenyl-s-hydraindacen-1 (2H)-one (2.48 g, 9.46 mmol) was dissolved in a 2:1 vol.;vol. mixture of tetrahydrofuran/methanol (20 mL) and sodium borohydride ($NaBH_4$, 0.54 g, 14.2 mmol) was slowly added. The reaction mixture was stirred overnight at room temperature. Water (50 mL) was added and the product extracted with diethyl ether (4×70 mL). The combined volumes were dried over $MgSO_4$ then dried under dynamic vacuum, leaving the product as a white solid. Yield, 2.46 g, 93 percent 1e) Preparation of N-(1,1-dimethylethyl)-1,1-dimethyl-1-(1,5,6,7-tetrahydro-2-methyl-4-phenyl-s-2-indacen-1-yl)silanamine

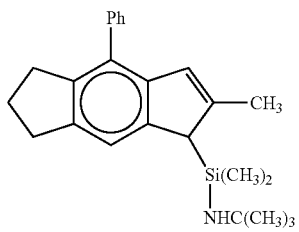

3,5,6,7-tetrahydro-2-methyl-4-phenyl-s-hydraindacen-1 (2H)-ol (2.46 g, 9.29 mmol) was dissolved in toluene (100 mL) and p-toluenesulfonic acid (0.12 g) was added. The resulting solution was heated to reflux for 3 hours, then washed with saturated aqueous $NaHCO_3$ (2×50 mL), dried over $MgSO_4$, filtered, and dried under dynamic vacuum, giving 2.0 g, 87 percent of the corresponding indacene.

A 125 mL glass flask was charged with the indacene (1.045 g) and 50 mL mixed hexanes. To this was then added 2.65 mL of n-butyllithium in mixed hexanes. After one hour, the mother liquor was decanted from the precipitate that had formed. The precipitate was dissolved in 30 mL of tetrahydrofuran (THF). To this solution, dimethyl(t-butylamino) silylchloride (0.800g in 5 mL THF) was added and the resulting mixture stirred overnight. The volatiles were removed under dynamic vacuum and the residue extracted with mixed hexanes (50 mL), filtered and the volatiles again removed under dynamic vacuum, giving 1.42 g (105 percent) of the desired product along with residual solvent.

1f) Preparation of dichloro[N-(1,1-dimethylethyl)-1,1-dimethyl-[1,2,3,3a,8a-η)-1,5,6,7-tetrahydro-2-methyl-4-phenyl-s-indacen-1-yl]silanaminato(2-)-N] titanium N-(1,1-dimethylethyl)-1,1-dimethyl-1-(1,5,6,7-tetrahydro-2-methyl-4-phenyl-s-indacen-1-yl)silanamine (1.42 g,) was stirred in hexane (30 mL) as n-BuLi (4.75 mL of a 1.6 M solution in mixed hexanes) was added dropwise. This mixture was then allowed to stir 1.5 hours. THF (30 mL) was added and the solution cooled to −30° C. Then $TiCl_3(THF)_3$ (1.4 g) was added with stirring as the mixture was warmed to room temperature. After 25 minutes $PbCl_2$ oxidant (1.5 g) was added and the mixture again stirred for 2 hours. The volatiles were removed under dynamic vacuum and the residue extracted with toluene (40 mL), filtered and the solids washed again with toluene. The filtrate was concentrated to dryness and washed repeatedly with mixed hexanes (50 mL) until no more colored product was extracted. The combined hexanes extracts were concentrated and the product recovered by recrystallization overnight at −30° C. and washing with cold hexanes. A second crop of crystals was recovered from the mother liquor after further washing with cold hexanes. Total yield was 1.1 g, 59 percent.

Example 2

Synthesis of [N-(1-dimethylethyl)-1,1-dimethyl-[1,2,3,3a,8a-η)-1,5,6,7-tetrahydro-2-methyl-4-phenyl-s-indacen-1-yl]silanaminato(2-)-N] titanium dimethyl

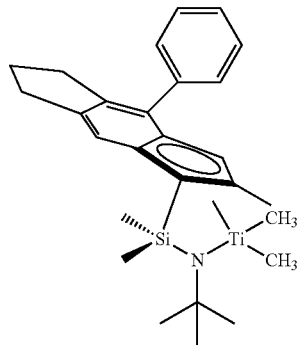

Dichloro[N-(1,1-dimethylethyl)-1,1-dimethyl-[1,2,3,3a,8a-η)-1,5,6,7-tetrahydro-2-methyl-4-phenyl-s-indacen-1-yl]silanaminato(2-)-N] titanium (0.25 g) in diethylether (15 mL) was cooled to −30° C. and 0.5 mL of a 3.0 M diethylether solution of methylmagnesium bromide was added. After 45 minutes reaction time the volatiles were removed under dynamic vacuum and the residue extracted with 15 mL of mixed hexanes. The extract was filtered and concentrated to dryness. The residue was again extracted into 10 mL of mixed hexanes, filtered and the volatiles removed under dynamic vacuum leaving the desired product as a glassy solid. Yield: 0.21 g, 91 percent.

Example 3

Synthesis of: dichloro[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminato(2-)-N] titanium

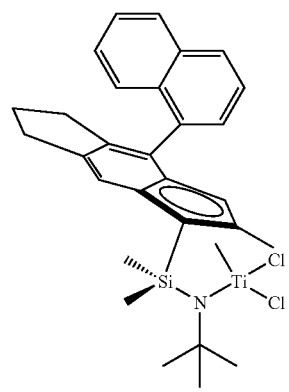

3a) Preparation of 3,5,6,7-tetrahydro-2-methyl-4-(1-naphthalenyl)-s-hydraindacen-1(2H)-one

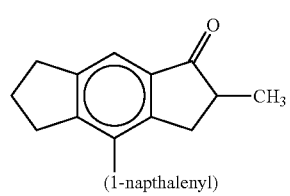

A 250-mL flask was charged with Pd(PPh3)4 (195 mg, 0.169 mmol), 1-naphthylboronic acid (4.13 g, 24 mmol), sodium carbonate (3.39 g, 32 mmol), 3,5,6,7-tetrahydro-2-methyl-4-bromo-s-hydraindacen-1(2H)-one from Example 1b (0.22 M in DME, 100 mL, 22 mmol), and water (30 mL). The resulting solution was heated at reflux for 16 hours. The DME was removed in vacuo, and the product extracted into diethyl ether (4×50 mL), dried (MgSO$_4$), filtered and evacuated to yield a tan semi-solid. Yield 6.97 g (100 percent).

3b) Preparation of 3,5,6,7-tetrahydro-2-methyl-4-(1-naphthalenyl)-s-hydraindacen-1(2H)-ol

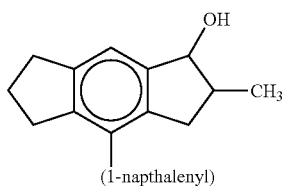

3,5,6,7-tetrahydro-2-methyl-4-(1-naphthalenyl)-s-hydraindacen-1(2H)-one (6.97 g, 22 mmol) was dissolved in a 2:1 mixture of THF and methanol (60 mL total), and sodium borohydride (1.25 g, 33.0 mmol) was added in portions. The dark brown solution was stirred at room temperature for 16 hours. Water (50 mL) was added, and the organic solvents removed in vacuo. The product was extracted with ether (3×150 mL) and dichloromethane (2×100 mL). The combined organic fractions were dried over MgSO$_4$, filtered, and the solvents removed in vacuo. The light gray solid obtained was dissolved in warm hexanes (50 mL), filtered through medium porosity filter paper, and the filtrate held in a −20° C. freezer. A white solid precipitated, and was collected by filtration and dried in vacuo. Yield 4.78 g (69.1 percent).

3c) Preparation of N-(1,1-dimethylethyl)-1,1-dimethyl-1-(1,5,6,7-tetrahydro-2-methyl-4-(1-naphthalenyl)-s-2-indacen-1-yl)silanamine

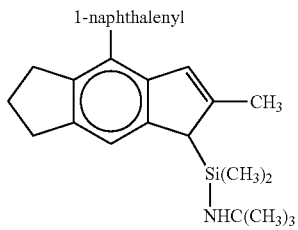

3,5,6,7-tetrahydro-2-methyl-4-(1-naphthalenyl)-s-hydraindacen-1(2H)-ol (4.78 g, 15.2 mmol) was dissolved in toluene (70 mL), and p-toluenesulfonic acid (0.25 g, 1.31 mmol) was added. The yellow solution was heated at reflux temperature with attached Dean-Stark trap. The solution darkened to a deep purple color. After 7 hours, the solution was cooled to room temperature, washed with saturated sodium bicarbonate solution (3×50 mL), dried over MgSO$_4$, filtered, and evacuated to yield 4.207 g (93.4 percent) of the neutral indacene as a brown oil. The product was lithiated by reaction with an equimolar quantity of butyl lithium in hexanes giving 3.055 g (71.2 percent) of a light yellow product. 0.80 g (2.65 mmol) Of the lithium salt was combined with 20 mL of THF followed by 0.5 g (2.91 mmol) of dimethyl(t-butylamino)silylchloride in 20 mL of THF. After stirring for three days, the volatiles were removed in vacuo and the residue extracted into 50 mL of hexanes, filtered and the volatiles removed in vacuo to leave 1.05 g (93 percent) of N-(1,1-dimethylethyl)-1,1-dimethyl-1-(1,5,6,7-tetrahydro-2-methyl-4-(1-naphthalenyl)-s-2-indacen-1-yl)silanamine in the form of a yellow oil.

3d) Dichloro[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminto(2-)-N] titanium To a 20 mL hexanes solution of 0.96 g (2.26 mmol) of N-(1,1-dimethylethyl)-1,1-dimethyl-1-(1,5,6,7-tetrahydro-2-methyl-4-(1-naphthalenyl)-s-2-indacen-1-yl)silanamine was added 2.82 mL of n-BuLi in hexanes (4.51 mmol, 1.6 M). After 30 minutes, the solution was diluted with 40 mL of THF and cooled to −30° C. To this was added 0.84 g (2.27 mmol) of TiCl$_3$(THF)$_3$ and the mixture allowed to stir and warm to room temperature. After 30 minutes, 1 g (3.5 mmol) of PbCl$_2$ and 10 mL of dichloromethane were added. The solution was stirred at room temperature overnight and the volatiles removed in vacuo. The residue was extracted into toluene, filtered and the volatiles removed in vacuo. The residue was extracted into hexanes and concentrated to 6 mL and cooled to −30° C. The obtained precipitate was collected and further purified by trituration with 5 mL of ether. The ether suspension was cooled to −30° C. and the obtained precipitate isolated, washed with 1 ml of cold ether and dried in vacuo to leave 250 mg (20 percent) of orange powder.

Example 4

Synthesis of: dimethyl[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminato(2-)-N] titanium

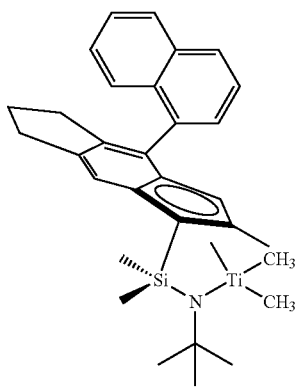

To a cooled (−30° C.) suspension of 0.090 g (0.17 mmol) of dichloro[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminato(2-)-N ] titanium in 5 mL of ether was added 0.20 mL of methylmagnesium bromide (0.5 mmol, 3.0 M). After 30 minutes, the volatiles were removed in vacuo, the residue extracted into 20 mL of hexanes, filtered and the volatiles removed in vacuo. The residue was extracted into hexanes (10 mL), filtered and the volatiles removed in vacuo to leave 0.060 g (72 percent) of a yellow solid.

Ethylene/1-Octene Copolymerization

A stirred 2 L reactor was charged with 740 g of mixed alkanes solvent and 118 g of 1-octene comonomer. Hydrogen was added as a molecular weight control agent by differential pressure expansion from a 75 mL addition tank at 25 psi (170 kPa). The reactor was heated to the polymerization temperature of 140° C. and saturated with ethylene at 500 psig (3.5 MPa). The desired quantity of metal complex (1.0 μmole for runs 1–3 and 9, 0.4 μmole for runs 4–6 and 11, 0.3 μmole for run 10 and 0.9 μmole for runs 7–8) and cocatalyst as 0.005 M solutions in toluene were premixed in a drybox in a 1:1 molar ratio, transferred to a catalyst addition tank and injected into the reactor over approximately a four minute period. The polymerization conditions were maintained for 15 minutes with ethylene on demand. The resulting solution was removed from the reactor, and a phosphorus stabilizer and hindered phenol antioxidant mixture (2:1 mixture of Irgafos™ 168 and Irganox™ 1010 from Ciba Geigy Corporation) was added to the resulting solution in approximate amounts equaling 200 mg/100 g polymer. The resulting polymer mixtures were dried in a vacuum oven set to achieve a maximum temperature of 120° C. over a 20 hour drying time. Results are contained in Table 1 and generally demonstrate increased octene incorporation in polymers produced with metal complexes according to the invention as evidenced by reduced density.

mL addition tank. The reactor is heated to 100° C. and saturated with ethylene at 500 psig (3.5 MPa). Metal complex as dilute toluene solution and cocatalyst as dilute solutions in toluene were mixed in a 1:1 molar ratio and transferred to a catalyst addition tank and injected into the reactor. The cocatalyst was methyldi(octadecyl)-ammonium tetrakis(pentafluoro-phenyl)borate (DAB), the ammonium cation of which is derived from a mixture of amines available commercially as methyl bis(tallow)amine. The polymerization conditions were maintained for 15 minutes with ethylene added on demand. The resulting solution was removed from the reactor, quenched with isopropyl alcohol, and stabilized by addition of a toluene solution containing 67 mg/100 g polymer of a hindered phenol antioxidant (Irganox™ 1010 from Ciba Geigy Corporation) and 133 mg/100 g polymer of a phosphorus stabilizer (Irgafos™ 168 from Ciba Geigy Corporation). Between sequential polymerization runs, a wash cycle was conducted in which 850

TABLE 1

| Run | Catalyst | Cocat. | Yield (g) | Eff.[1] | Density[2] | MI[3] | Mw | PD[4] |
|---|---|---|---|---|---|---|---|---|
| 1 | Ex. 2 | FAB[5] | 89.0 | 1.86 | 0.880 | 3.6 | — | — |
| 2 | " | " | 88.8 | 1.85 | 0.879 | 3.9 | 69,000 | 3.0 |
| 3* | MTM[6] | " | 40.1 | 0.84 | 0.889 | 0.6 | 139,000 | 2.3 |
| 4 | Ex. 2 | DAB[7] | 115.3 | 6.02 | 0.873 | 5.8 | 78,000 | 2.3 |
| 5 | " | " | 105.5 | 5.51 | 0.875 | 4.6 | 80,000 | 2.3 |
| 6* | MTM[6] | " | 67.6 | 3.53 | 0.884 | 0.4 | 146,000 | 2.1 |
| 7 | Ex. 4 | FAB[5] | 100.6 | 2.33 | 0.873 | 2.7 | — | — |
| 8 | " | " | 103.6 | 2.40 | 0.871 | 3.1 | 93,800 | 2.3 |
| 9* | MTM[6] | " | 62.9 | 1.31 | 0.883 | 0.6 | — | — |
| 10 | Ex. 4 | DAB[7] | 93.7 | 6.52 | 0.870 | 2.7 | 98,800 | 2.3 |
| 11* | MTM[6] | " | 36.2 | 1.89 | 0.886 | 0.5 | — | — |

*comparative, not an example of the invention
[1] grams polymer per μg Ti
[2] g/ml
[3] melt index $I_2$ dg/min (ASTM-D-1238-E)
[4] polydispersity Mw/Mn
[5] tris(pentafluorophenyl)borane
[6] [N-(1,1-dimethylethyl)-1,1-dimethyl-[1,2,3,3a,8a-η)-1,5,6,7-tetrahydro-2-methyl-s-indacen-1-yl]silanaminato(2-)-N] titanium dimethyl prepared according to U.S. Pat. No. 5,965,756.
[7] di(octadecyl)methylammonium tetrakis(pentafluorophenyl)borate Ethylene/1-Octene/Ethylidenenorbornene Polymerization Conditions All liquids except ethylidenenorbornene (ENB) and gas feeds were passed through columns of alumina and a decontaminant (Q-5™ catalyst available from Englehardt Chemicals Inc.) prior to introduction into the reactor. ENB was passed through a short column (3×10 cm) of alumina prior to introduction to the reactor. Catalyst components are handled in a glovebox containing an atmosphere of argon or nitrogen. A stirred 2.0 liter reactor is charged with 640 g of mixed alkanes solvent, 150 g of 1-octene and 16 g of ENB. Hydrogen (20 psi, 140 kPa) is added as a molecular weight control agent by differential pressure expansion from a 75 g of mixed alkanes was added to the reactor and the reactor was heated to 130° C. The reactor was then emptied of the heated solvent immediately before beginning a new polymerization run.

Polymers were recovered by drying in a vacuum oven set at 140° C. for 20 hours. Density values are derived by determining the polymer's mass when in air and when immersed in methylethyl ketone. GPC results are determined by standard methods and are reported relative to a polystyrene/polyethylene universal calibration. The percent ethylene, octene and ENB for the polymer were determined by $^{13}$C NMR analysis of the material. Results are contained in Table 2.

TABLE 2

| Run | Catalyst | Yield (g) | Eff.[1] | Density (g/ml) | Mw (×10³) | Mw/Mn | percent octene | percent ENB |
|---|---|---|---|---|---|---|---|---|
| 12 | Ex. 2 (0.9 μmol) | 68.6 | 1.59 | 0.868 | 240 | 2.2 | 41 | 2.6 |
| 13* | MTM[2] (1 μmol) | 53.3 | 1.11 | 0.881 | 347 | 2.1 | 32 | 2.8 |

[1] efficiency, g polymer/μg titanium
[2] [N-(1,1-dimethylethyl)-1,1-dimethyl-[1,2,3,3a,8a-η)-1,5,6,7-tetrahydro-2-methyl-s-indacen-1-yl]silanaminato(2-)-N]titanium dimethyl
*comparative, not an example of the invention

The invention claimed is:

1. A metal complex corresponding to the formula (I):

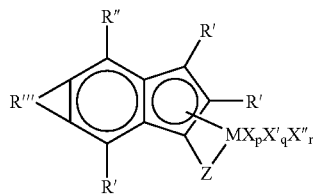

where M is titanium, zirconium or hafnium in the +2, +3 or +4 formal oxidation state;

R' independently each occurrence is hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl) amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' group having up to 40 nonhydrogen atoms, and optionally two or more of the foregoing groups may together form a divalent derivative;

R" independently each occurrence is a $C_{6-12}$ aryl group;

R''' is a divalent hydrocarbylene- or substituted hydrocarbylene group forming a fused system with the remainder of the metal complex, said R''' containing from 1 to 30 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

2. The metal complex of claim 1 corresponding to the formula (II):

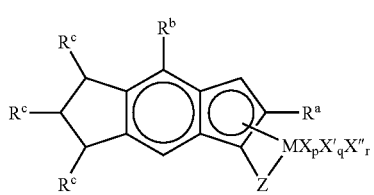

where M is titanium, zirconium or hafnium in the +2, +3 or +4 formal oxidation state;

$R^a$ independently each occurrence is hydrogen, $C_{1-10}$ alkyl, aralkyl or cycloalkyl, preferably methyl or benzyl;

$R^b$ is a $C_{6-12}$ aryl group;

$R^c$ independently each occurrence is hydrogen, $C_{1-6}$ alkyl, or cycloalkyl, preferably each occurrence $R^c$ is hydrogen;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

3. The metal complex of claim 2 corresponding to the formula:

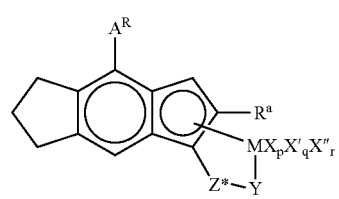

wherein:

$A^R$ is phenyl or naphthalenyl;

$R^a$ is methyl or benzyl;

M is titanium;

Y is —O—, —S—, —NR*—, —PR*—; —NR$_2$*, or —PR$_2$*;

Z* is SiR*$_2$, CR*$_2$, SiR*$_2$SiR*$_2$, CR*$_2$CR*$_2$, CR*═CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 24 non-hydrogen atoms, and optionally, two R* groups from Z (when R* is not hydrogen), or an R* group from Z and an R* group from Y form a ring system;

X, X' and X" are as previously defined in claim 2;

p is 0, 1 or 2;

q is zero or 1; and r is zero or 1; and when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms, when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

4. The metal complex of claim 3 which is:

dichloro[N-(1,1-dimethylethyl)-1,1-dimethyl-[1,2,3,3a,8a-η)-1,5,6,7-tetrahydro-2-methyl-4-phenyl-s-indacen-1-yl]silanaminato(2-)-N] titanium,

[N-(1,1-dimethylethyl)-1,1-dimethyl-[1,2,3,3a,8a-η)-1,5,6,7-tetrahydro-2-methyl-4-phenyl-s-indacen-1-yl]silanaminato(2-)-N] titanium dimethyl;

dichloro[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminato(2-)-N] titanium, or

[N-(1,1-dimethylethyl)-1,1-dimethyl-[1,2,3,3a,8a-η)-1,5,6,7-tetrahydro-2-methyl-4-(1-naphthalenyl)-s-indacen-1-yl]silanaminato(2-)-N] titanium dimethyl.

5. A process for the polymerization of olefins comprising contacting one or more olefins under polymerization conditions with a catalyst composition comprising one or more metal complexes of any one of claims 1–4.

6. A process according to claim 5 wherein ethylene and one or more $C_{3-8}$ α-olefins or styrene and optionally a conjugated or non-conjugated diene are polymerized.

* * * * *